United States Patent
Chawla (10) Patent No.: US 9,962,092 B1
(45) Date of Patent: May 8, 2018

(54) CLINICAL THERMOMETER

(71) Applicant: Surbhi Chawla, Hong Kong (CN)

(72) Inventor: Surbhi Chawla, Hong Kong (CN)

(73) Assignee: Surbhi Chawla, Hong Kong (CN)

( * ) Notice: Subject to any disclaimer, the term of this patent is extended or adjusted under 35 U.S.C. 154(b) by 0 days. days.

(21) Appl. No.: 15/709,491

(22) Filed: Sep. 20, 2017

Related U.S. Application Data (63) Continuation of application No. 15/629,756, filed on Jun. 22, 2017.

(51) Int. Cl.
*A61B 5/00* (2006.01)
*A61B 5/01* (2006.01)
*G01K 1/02* (2006.01)
*G01K 13/00* (2006.01)

(52) U.S. Cl.
CPC .............. *A61B 5/01* (2013.01); *G01K 1/024* (2013.01); *G01K 13/002* (2013.01)

(58) Field of Classification Search
CPC ......... A61B 5/01; G01K 1/024; G01K 13/002
USPC ....................................................... 600/549
See application file for complete search history.

(56) References Cited

U.S. PATENT DOCUMENTS

| | | | |
|---|---|---|---|
| 6,497,657 B2 * | 12/2002 | Nunome | A61B 5/0002 128/904 |
| 7,350,973 B2 | 4/2008 | Craig et al. | |
| 8,808,178 B2 * | 8/2014 | Lane | A61B 5/01 128/920 |
| 9,592,033 B2 * | 3/2017 | Toriumi | A61B 5/746 |
| 9,693,689 B2 * | 7/2017 | Gannon | A61B 5/0008 |
| 9,795,305 B2 * | 10/2017 | Mullin | A61B 5/01 |
| 9,801,543 B2 * | 10/2017 | Gross | H04W 80/04 |

FOREIGN PATENT DOCUMENTS

WO      0133178      5/2001

OTHER PUBLICATIONS

Kaz Europe Sarl, Braun Age Precision Digital Thermometer Instruction Manual, 2014, 1-7.

* cited by examiner

*Primary Examiner* — Max Hindenburg
(74) *Attorney, Agent, or Firm* — Eagle IP Limited; Jacqueline C. Lui (57) ABSTRACT

A thermometer that displays written instructions that instruct a person what action to take based on a sensed temperature. The thermometer includes a temperature sensor that senses a temperature of a person and a display that provides written instructions that inform the person what action to take based on their temperature.

20 Claims, 6 Drawing Sheets

CLINICAL THERMOMETER

FIELD OF THE INVENTION

The present invention relates to a thermometer for detecting a person's temperature and providing instructions to the user based on the temperature.

BACKGROUND

A rise in a person's temperature is usually indicative of an illness. Thermometers are commonly used to check if a person's temperature is elevated. Advancements in thermometers will help people who have elevated temperatures.

SUMMARY OF THE INVENTION

One example embodiment is a thermometer that displays a person's temperature and written instructions that instruct the person what action to take based on the sensed temperature. The thermometer includes a temperature sensor that senses the temperature of the person and a display. The display provides written instructions that inform the person what action to take based on their temperature.

Other example embodiments are discussed herein.

DETAILED DESCRIPTION

One problem with conventional thermometers is that they typically provide the person with no information other than the sensed temperature. This information can be sufficient for an experienced health care provider or doctor, but not for other individuals. Many people in developing countries do not know which temperature readings are good or acceptable and which ones are dangerous for the person. Further, an adolescent or elderly person may not be familiar with different temperature readings. What action should a person take when the temperature reading is, for example, 99.3° Fahrenheit or 37.8° Celsius? When is a temperature high enough to take no action or high enough to see a doctor? When is a temperature high enough to constitute an immediate medical emergency for a person? What action should a person take after reading any temperature that is above normal? Example embodiments solve these problems associated with conventional thermometers.

Example embodiments relate to apparatus and methods that provide a thermometer that includes a temperature sensor and a display. The display provides a temperature of a person and a written instruction that informs the person what action to take based on the sensed temperature.

The display provides different written instructions for a normal temperature, an elevated temperature, and a dangerous elevated temperature. Based on the sensed or recorded temperature, the thermometer provides written or audible instructions on what action the person should take.

In one example embodiment, the written instruction includes text that instructs the person to seek medical assistance when the temperature of the person is elevated. In one example embodiment, the temperature of the person and the written instruction are simultaneously displayed on the display.

In one example embodiment, the instructions are announced to the person with a sound chip inside the thermometer. Immediately after sensing or recording the temperature, the thermometer announces verbal instructions or recommendations on what actions the person should take based on the sensed temperature. These verbal instructions can be separate or in addition to the written instructions.

One example embodiment includes a memory that stores different temperature ranges and different written and/or verbal instructions for each of the different temperature ranges to visually and/or audibly instruct the person on what action is necessary based on their temperature. One example embodiment includes a memory that stores a threshold temperature that instructs the person to go to a hospital when the temperature of the person exceeds the threshold temperature. One example embodiment includes a memory that stores three different temperature ranges and a different instruction for each of the three temperature ranges.

In one example embodiment, the three temperature ranges and three written and/or audible instructions include a first temperature range for a normal temperature and a first written and/or audible instruction that informs the person that no action is necessary, a second temperature range for an elevated temperature and a second written and/or audible instruction that informs the person to see a doctor, and a third temperature range for a dangerous elevated temperature, that is higher than the elevated temperature range, and a third written and/or audible instruction that informs the person to go to a hospital. In one example embodiment, the second written and/or audible instruction includes "SEE DOCTOR", and the third written and/or audible instruction includes "GO TO HOSPITAL". In other example embodiments, the written and/or audible instructions include "TAKE MEDICATION", "DANGER SEE DOCTOR", "NORMAL—CONTINUE TO MONITOR", "ELEVATED—SEE DOCTOR", "FEVER—GO TO HOSPITAL", "SEEK MEDICAL ADVICE", and "CONSULT DOCTOR".

In one example embodiment, the first written instruction is provided in a green color when the temperature of the person is normal, in a yellow or amber color when the temperature of the person is in a first elevated range, and in a red color when the temperature of the person is in a second elevated temperature range that is higher than the first elevated temperature range.

In one example embodiment, the thermometer includes a user interface (UI) that receives input from the person to select their preferred language for the written instructions from a plurality of different languages.

In one example embodiment, the thermometer includes a sound chip that speaks the instructions to the person so the person can hear what action to take based on the person's temperature.

One example embodiment includes a controller that receives the temperature of the person from the temperature sensor and performs a comparison of the temperature of the person with the temperature ranges stored in the memory. The controller selects one of the temperature ranges based on the comparison and selects the written and/or verbal instruction corresponding to the selection of one of the temperature ranges. The controller provides the selection of the chosen instruction to the display. In one particular example embodiment, the controller compares the temperature of the person from the temperature sensor with three different temperature ranges stored in the memory.

One example embodiment includes a light emitting device. The light emitting device communicates with the controller and emits light in a plurality of colors based on the temperature of the person. In one example embodiment, the light emitting device emits three different color lights. The first color light indicates a normal temperature; the second color light indicates an elevated temperature; and a third color light indicates fever conditions.

In one example embodiment, the display simultaneously displays word instructions and either the first color light, second color light, or third color light.

In one example embodiment, the thermometer simultaneously announces or speaks the instructions to the person and displays either the first color light, second color light, or third color light.

In one example embodiment, the thermometer simultaneously announces or speaks the instructions to the person, displays instructions being spoken to the person, and displays either the first color light, second color light, or third color light.

Figure 1:
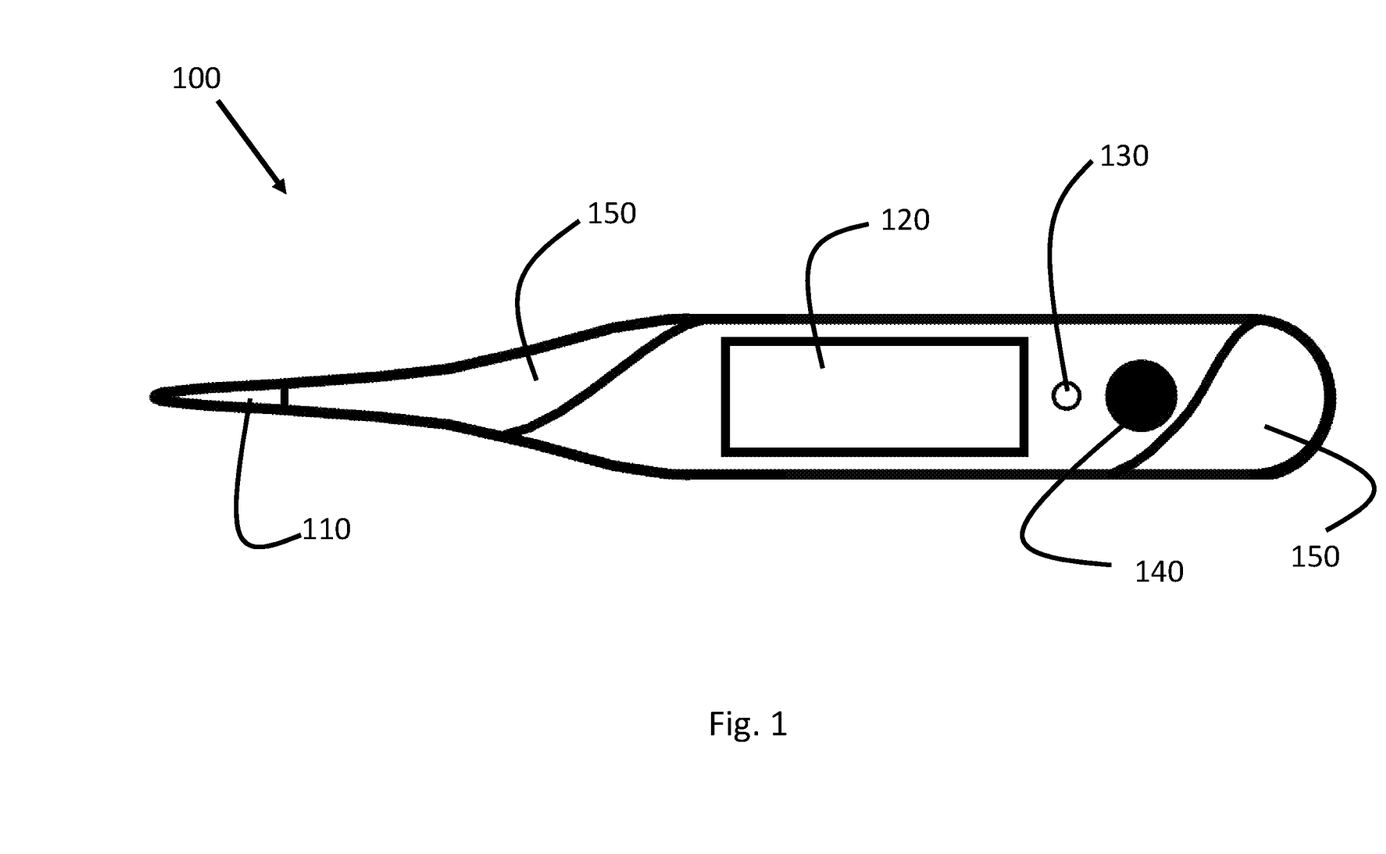
FIG. 1 shows a top view of a thermometer in accordance with an example embodiment.

FIG. 1 shows a thermometer 100 that includes a temperature sensor 110, a display 120, a light emitting device 130, and an on/off button 140 in accordance with an example embodiment. In an example embodiment the ends of the thermometer 150 are encased in colored rubber.

The display 120 provides the written instructions to the person and can also function as a user interface (UI). For example, the display provides menu selections that enable the user to select readings in Celsius or Fahrenheit or to select written or audible instructions in a particular language (such as selecting among English, Chinese, Spanish, French, German, etc.).

Figure 2:
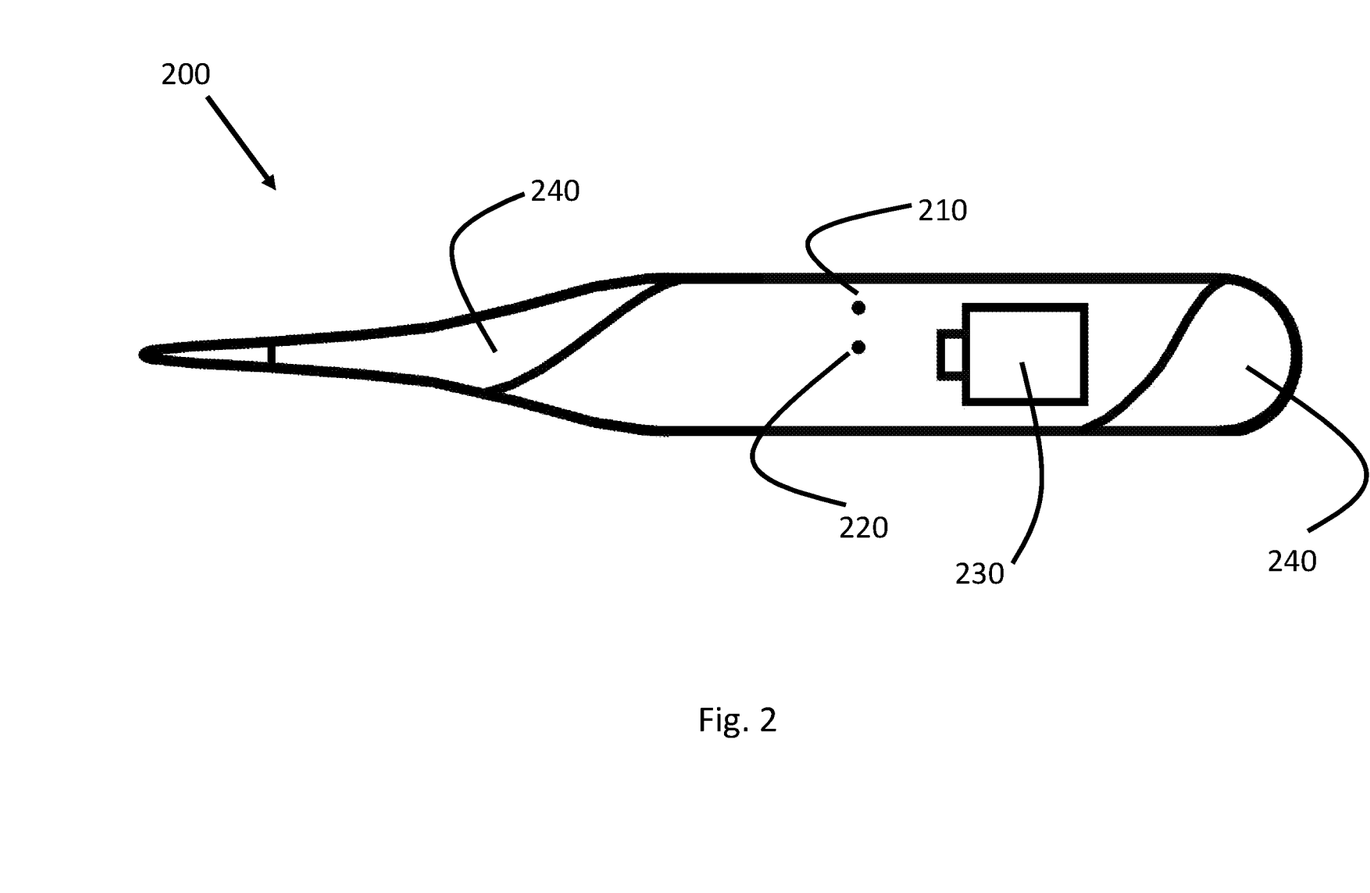
FIG. 2 shows a bottom view of a thermometer in accordance with an example embodiment.

FIG. 2 shows a thermometer 200 that includes a ° C./° F. conversion button 210, a reset button 220, and a battery compartment 230 in accordance with an example embodiment. In another example embodiment the ends of the thermometer 240 are encased in colored rubber.

Figure 3:
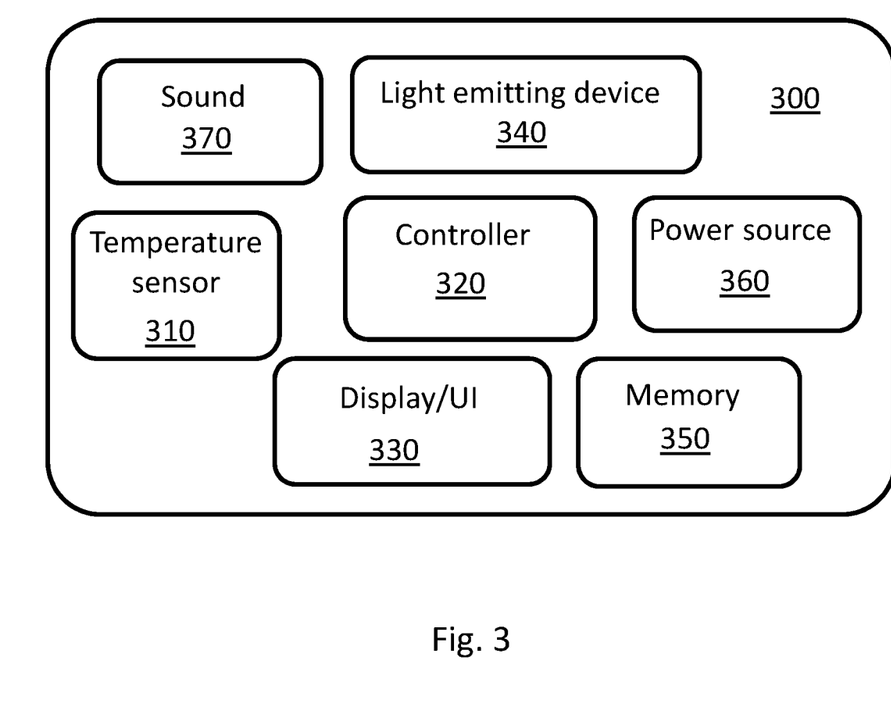
FIG. 3 shows different electronic components of a thermometer in accordance with an example embodiment.

FIG. 3 shows different components of a thermometer 300 in accordance with an example embodiment. The thermometer 300 includes a temperature sensor 310, a controller 320, a display and/or user interface (UI) 330, a light emitting device 340, a memory 350, a power source 360, and sound 370.

The power source 360 provides power to one or more components in the thermometer and includes, for example, a removable or replaceable battery.

The controller 320 receives the temperature from the temperature sensor 310, and communicates with the memory 350 and the display 330 to display a written instruction and/or announce an audible instruction corresponding to a temperature range and instruction stored in the memory 350. In an example embodiment, the controller 320 communicates with the memory 350, the display 330 and the light emitting device 340 to display the written instruction on the display 330 and to illuminate the light emitting device 340 to emit a colored light based on the temperature of the person. By way of example, the different colored lights include green, yellow, amber and red, with each color being assigned to indicate the temperature range of the person.

By way of example, sound 370 includes one or more of a sound chip, an amplifier, and a speaker. Controller 320 communicates with the sound chip to announce prerecorded or stored audible instructions, such as "go to the doctor" or "seek medical assistance" or another instruction discussed herein.

Figure 4:
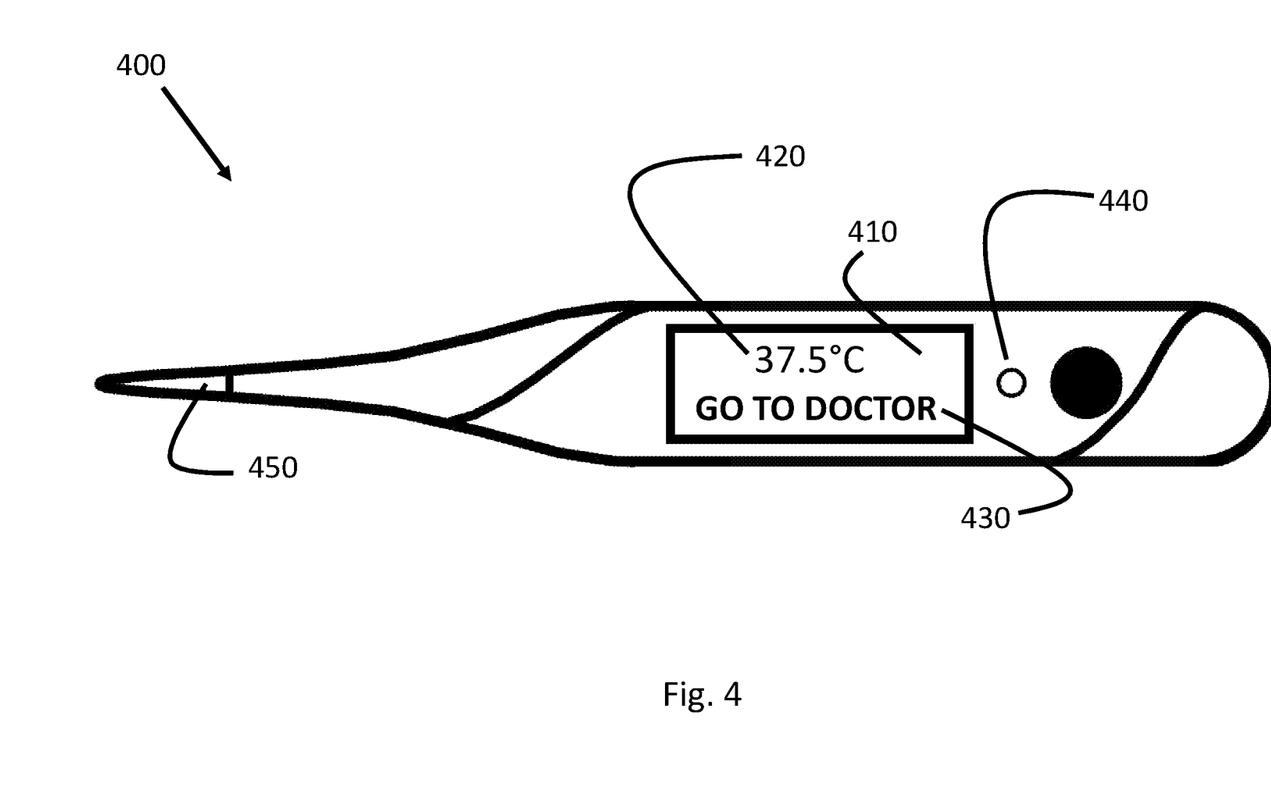
FIG. 4 shows a thermometer with a display providing a temperature of a person and a written instruction in accordance with an example embodiment.

FIG. 4 shows a thermometer 400 with a display 410 displaying the temperature of the person 420 and the written instruction 430 telling the person what action to take based on the temperature 420 as detected by the temperature sensor 450 in accordance with an example embodiment.

In an example embodiment, the temperature of the person 420 and the written instruction 430 are displayed on the display 410 simultaneously.

In another example embodiment, a light emitting device 440 emits a different color light based on the temperature of the person 420 as measured by the temperature sensor 450. In an example embodiment, the light emitting device 440 emits a colored light and the display 410 displays the temperature of the person 420 and the written instruction 430 simultaneously. By way of example, the different colored light emitted by the light emitting device 440 include green, yellow, amber and red, with each color being assigned to indicate the temperature of the person 420.

In an example embodiment, the written instruction 430 includes text that instructs the person to seek medical assistance when the temperature of the person 420 is elevated. By way of example, the written instruction 430 includes "SEE DOCTOR", "GO TO HOSPITAL", "TAKE MEDICATION", "DANGER SEE DOCTOR", "CONSULT DOCTOR", "NORMAL—CONTINUE TO MONITOR", "ELEVATED—SEE DOCTOR", and "FEVER—GO TO HOSPITAL". These written instructions can also be announced to the person with the sound chip.

In another example embodiment, the person may choose which language the written instruction 430 is displayed in from a plurality of different languages.

In another example embodiment, the written instruction 430 is provided in different colors according to the person's temperature range. By way of example, a first written instruction is provided in a color of green when the temperature of the person 420 is normal, a second written instruction is provided in a color of yellow or amber when the temperature of the person 420 is in a first elevated temperature range, and a third written instruction is provided in a color of red when the temperature of the person 420 is in a second elevated temperature range that is higher than the first elevated temperature range.

Figure 5:
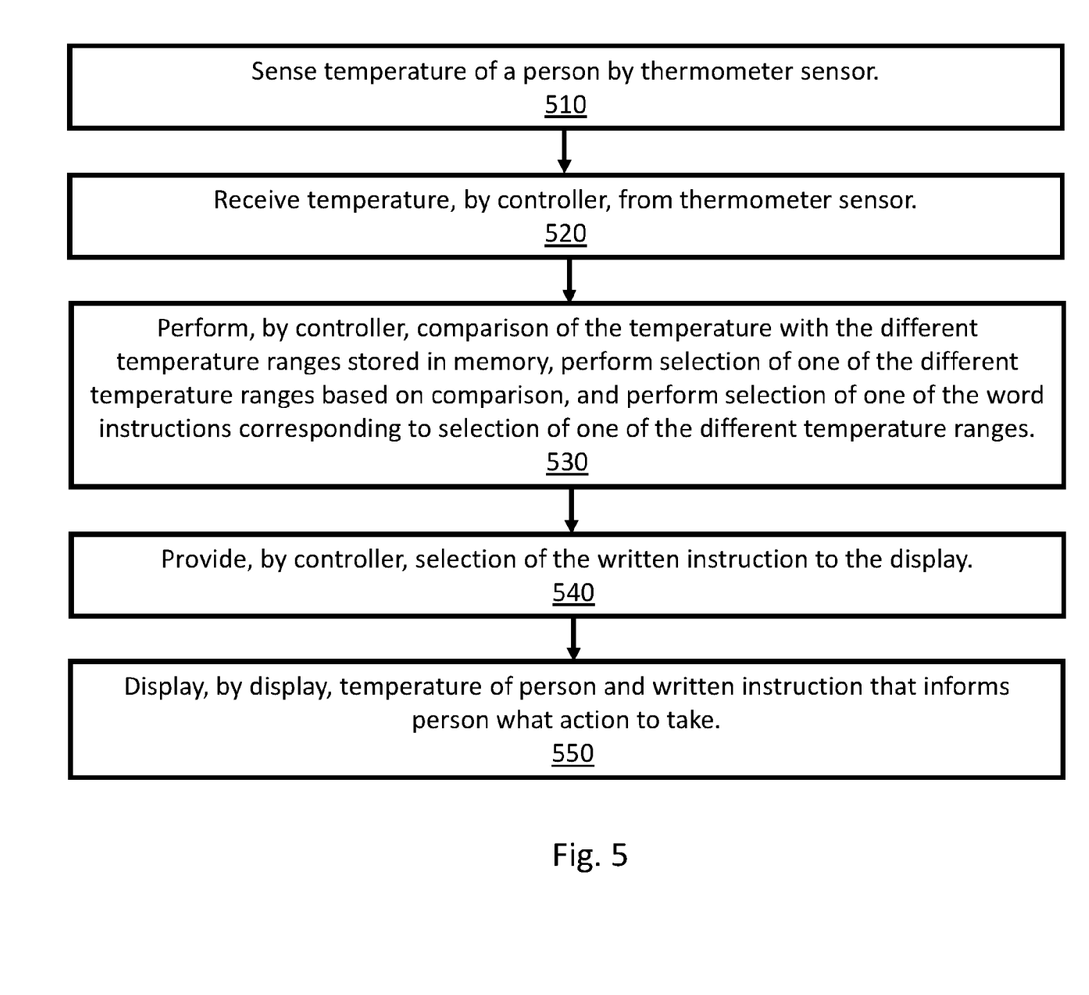
FIG. 5 shows a method executed by a thermometer of detecting a person's temperature and providing written instructions of what action to take based on the person's temperature in accordance with an example embodiment.

FIG. 5 shows a method executed by a thermometer of detecting a person's temperature and providing written instructions on what action to take based on the person's temperature in accordance with an example embodiment.

A temperature of a person is sensed by a temperature sensor 510.

The temperature is received by a controller from the temperature sensor 520.

A comparison of the temperature received 520 with different temperature ranges stored in a memory is performed by the controller, a selection of one of the temperature ranges based on the comparison is performed by the controller, and a selection of one of the written instructions corresponding to the selection of one of the temperature ranges is performed by the controller 530.

A selection of the written instruction is provided to the display by the controller 540.

The temperature of the person and the written instruction informing the person what action to take based on their temperature is displayed on the display 550.

In an example embodiment, the temperature of the person and the written instruction are displayed simultaneously. Further, as noted herein, the written instruction can be announced to the person.

In an example embodiment, the memory stores a first temperature range for a normal temperature and a first written instruction that informs the person that no action is necessary, a second temperature range for an elevated temperature and a second written instruction that informs the person to see a doctor, and a third temperature range for a dangerous elevated temperature and a third written instruction that informs the person to go to a hospital. In another example embodiment, the first temperature range is 36.1° C.-37.2° C. or 96.98° F.-98.96° F. and the first written instruction is "NORMAL—CONTINUE TO MONITOR", the second temperature range is 37.3° C.-39.3° C. or 99.14° F.-102.74° F. and the second written instruction is "ELEVATED—SEE DOCTOR", and the third temperature range of greater than 39.4° C. or 102.92° F. and the third written instruction is "FEVER—GO TO HOSPITAL".

In another example embodiment, the first written instruction is provided in a green color indicating the temperature of the person is normal, the second written instruction is provided in a yellow or amber color indicating the temperature of the person is in a first elevated temperature range, and the third written instruction is provided in a red color indicating the temperature of the person is in a second elevated temperature range that is higher than the first elevated temperature range.

Figure 6:
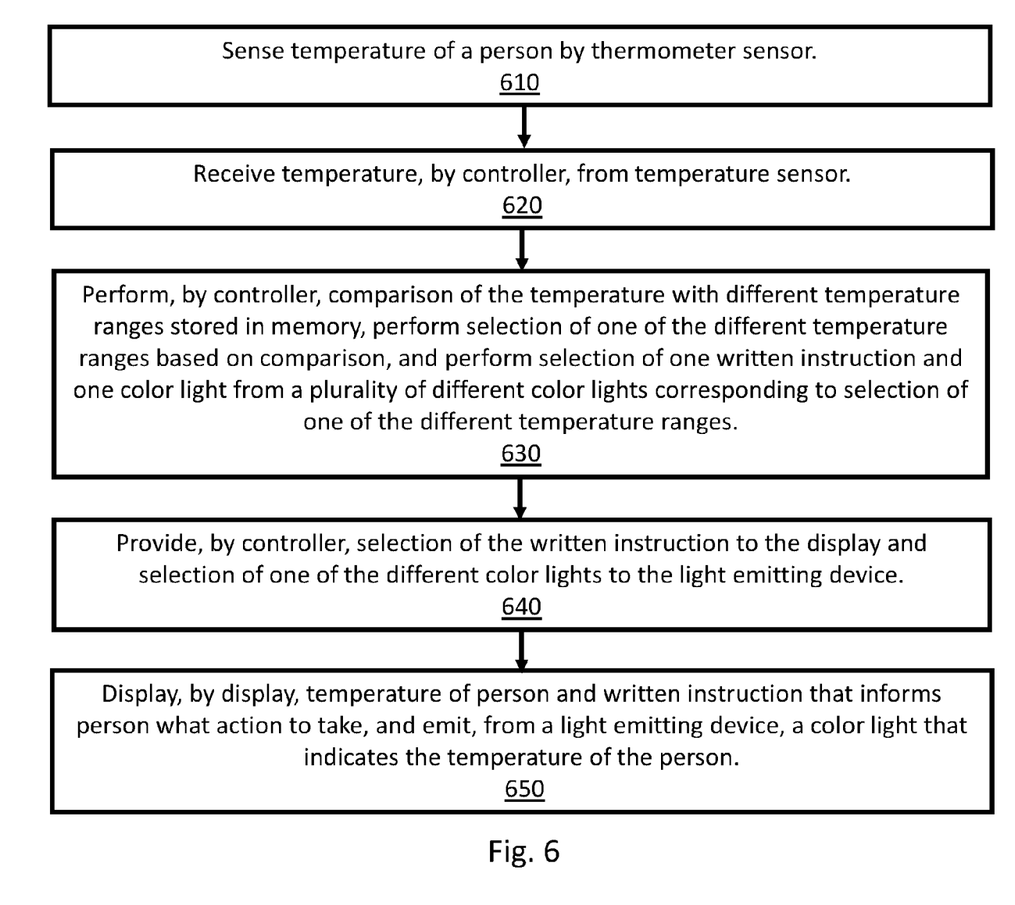
FIG. 6 shows a method executed by a thermometer of detecting a person's temperature, providing written instructions of what action to take based on the person's temperature, and emitting a colored light in accordance with an example embodiment.

FIG. 6 shows a method executed by a thermometer of detecting a person's temperature, providing written instructions on what action to take based on the person's temperature and emitting a color light in accordance with an example embodiment.

A temperature of a person is sensed by a temperature sensor 610.

The temperature is received by a controller from the temperature sensor 620.

A comparison of the temperature received 620 with different temperature ranges stored in a memory is performed by the controller, a selection of one of the temperature ranges based on the comparison is performed by the controller, and a selection of one of the written instructions and one color light from a plurality of different color lights corresponding to the selection of one of the temperature ranges is performed by the controller 630.

A selection of the written instruction is provided to the display, and a selection of one of the different color lights is provided to the light emitting device by the controller 640.

The temperature of the person and the written instruction informing the person what action to take based on their temperature is displayed on the display by the display, and a color light corresponding to the temperature of the person is emitted by a light emitting device 650.

In an example embodiment, the temperature of the person, the written instruction and the color light corresponding to the temperature of the person are displayed and emitted simultaneously.

In an example embodiment, there are three temperature ranges, three written instructions and three different color lights. In another example embodiment, when the temperature of the person is within a first temperature range of 36.1° C.-37.2° C. or 96.98° F.-98.96° F., a first written instruction of "NORMAL—CONTINUE TO MONITOR" is displayed and a first color light is emitted, when the temperature of the person is within a second temperature range of 37.3° C.-39.3° C. or 99.14° F.-102.74° F., a second written instruction of "ELEVATED—SEE DOCTOR" is displayed and a second color light is emitted, when the temperature of the person is within a third temperature range of greater than 39.4° C. or 102.92° F., a third written instruction of "FEVER—GO TO HOSPITAL" is displayed and a third color light is emitted.

In an example embodiment, the memory stores a first temperature range for a normal temperature and a first written instruction that informs the person that no action is necessary, a second temperature range for an elevated temperature and a second written instruction that informs the person to see a doctor, and a third temperature range for a dangerous elevated temperature and a third written instruction that informs the person to go to a hospital. In another example embodiment, the first temperature range is 36.1° C.-37.2° C. or 96.98° F.-98.96° F. and the first written instruction is "NORMAL—CONTINUE TO MONITOR", the second temperature range is 37.3° C.-39.3° C. or 99.14° F.-102.74° F. and the second written instruction is "ELEVATED—SEE DOCTOR", and the third temperature range is greater than 39.4° C. or 102.92° F. and the third written instruction is "FEVER—GO TO HOSPITAL".

Example embodiments disclosed herein provide various examples of written and verbal instructions, such as "Go to the hospital," "See a doctor," "Seek medical assistance," "Continue to monitor your temperature," and other instructions provided herein. One of ordinary skill in the art will appreciate that these instructions are merely examples. Other verbal and written instructions can be provided by the thermometer without departing from the scope of this invention.

As used herein, a "written instruction" provides writing that instructs a person on what action the person should take based on the sensed temperature.

Writing includes words and may include one or more characters or symbols in addition to the words.

As used herein, an "audible instruction" provides spoken language that instructs a person on what action the person should take based on the sensed temperature. Spoken language includes human speech.

What is claimed is:
1. A thermometer, comprising:
a temperature sensor that senses a temperature of a person;
a display that provides the temperature of the person and a written instruction that informs the person what action to take based on the temperature of the person; and
a memory that stores a first temperature range for a normal temperature and a first written instruction that informs the person that no action is necessary, a second temperature range for an elevated temperature and a second written instruction that informs the person to see a doctor, and a third temperature range for a dangerous elevated temperature and a third written instruction that informs the person to go to a hospital.

2. The thermometer of claim 1, wherein the temperature of the person and the written instruction are simultaneously displayed on the display.

3. A thermometer, comprising:
a temperature sensor that senses a temperature of a person;
a display that provides the temperature of the person and a written instruction that informs the person what action to take based on the temperature of the person;
a memory that stores three different temperature ranges and a different written instruction for each of the three different temperature ranges; and
a controller that receives the temperature of the person from the temperature sensor, performs a comparison of the temperature of the person with the three different temperature ranges stored in the memory, performs a selection of one of the three different temperature ranges based on the comparison, performs a selection of the written instruction corresponding to the selection of the one of the three different temperature ranges, and provides the selection of the written instruction to the display.

4. The thermometer of claim 1, wherein the written instruction includes text that instructs the person to seek medical assistance when the temperature of the person is elevated.

5. The thermometer of claim 1, wherein the memory stores a threshold temperature and the written instruction includes text that instructs the person to go to a hospital when the temperature of the person is greater than the threshold temperature.

6. The thermometer of claim 1, wherein the first written instruction is provided in a color of green when the temperature of the person is normal, in a color of yellow or amber when the temperature of the person is in the second elevated temperature range, and in a color of red when the temperature of the person is in the third dangerous elevated temperature range that is higher than the second elevated temperature range.

7. The thermometer of claim 1, wherein the written instruction includes "SEE DOCTOR" when the temperature of the person is within the second temperature range.

8. The thermometer of claim 1, wherein the written instruction includes "GO TO HOSPITAL" when the temperature of the person is within the third temperature range.

9. The thermometer of claim 1, further comprising:
a light emitting device that emits light in a plurality of different colors based on the temperature of the person.

10. The thermometer of claim 1, further comprising:
a user interface (UI) that receives input from the person to select from a plurality of different languages for the written instructions that instruct the person.

11. The thermometer of claim 9, wherein the light emitting device emits a first color light that indicates a normal temperature, a second color light that indicates an elevated temperature, and a third color light that indicates fever conditions, and wherein the display simultaneously displays written instructions and one of the first color light, the second color light, and the third color light.

12. The thermometer of claim 1 further comprising:
a sound chip that speaks the written instructions to the person.

13. The thermometer of claim 1, wherein the written instructions include "TAKE MEDICATION" displayed on the display.

14. The thermometer of claim 1, wherein the written instructions include "DANGER SEE DOCTOR" displayed on the display.

15. The thermometer of claim 1, wherein the written instructions include "CONSULT DOCTOR" displayed on the display.

16. The thermometer of claim 1, wherein the first temperature range is 36.1° C.-37.2° C. or 96.98° F.-98.96° F.

17. The thermometer of claim 1, wherein the second temperature range is 37.3° C.-39.3° C. or 99.14° F.-102.74° F.

18. The thermometer of claim 1, wherein the third temperature range is greater than 39.4° C. or 102.92° F.

19. The thermometer of claim 3, wherein the memory stores a threshold temperature for each of the temperature ranges and the written instruction includes text that informs the person on what action to take when the temperature of the person is greater than the threshold temperature.

20. The thermometer of claim 3, wherein the temperature of the person and the written instruction are simultaneously displayed on the display.

* * * * *